United States Patent [19]

Kóródi et al.

[11] Patent Number: 5,104,884
[45] Date of Patent: Apr. 14, 1992

[54] TRIAZOLYL QUINOLINE DERIVATIVES

[75] Inventors: Ferenc Kóródi; László Frank; Zoltán SalamAUC/o/ n, all of Tiszavasvári; József Sándor, Tiszalök; Emma Pocsai; Erzsébet Terebes, both of Tiszavasvári, all of Hungary

[73] Assignee: Alkaloida Vegyészeti Gyár, Tiszavasvári, Hungary

[21] Appl. No.: 219,903

[22] Filed: Jul. 13, 1988

Related U.S. Application Data

[63] Continuation of Ser. No. 6,651, filed as PCT/HU86/00026, May 7, 1986, abandoned.

[30] Foreign Application Priority Data

May 7, 1985 [HU] Hungary .................. 1718/85

[51] Int. Cl.$^5$ ............... A01N 43/653; C07D 401/04; C07D 401/12
[52] U.S. Cl. ................................ 514/312; 514/313; 546/153; 546/156; 546/157; 546/162
[58] Field of Search ........... 546/153, 157, 167, 156, 546/176, 177, 159, 162; 514/314, 312, 313

[56] References Cited

U.S. PATENT DOCUMENTS

| | | | |
|---|---|---|---|
| 3,769,411 | 10/1973 | Seidel et al. | 514/383 |
| 4,146,716 | 3/1979 | Cox et al. | 544/278 |
| 4,659,720 | 4/1987 | Chabala et al. | 546/162 |
| 4,772,613 | 9/1988 | Parsons et al. | 546/153 |

FOREIGN PATENT DOCUMENTS

| | | |
|---|---|---|
| 115049 | 8/1984 | European Pat. Off. |
| 1358893 | 7/1974 | United Kingdom |

OTHER PUBLICATIONS

Kauffmann et al., Chemical Abstracts, vol. 77, No. 152073 (1972).
Advanced Organic Chemistry (2nd. Ed.) by Jerry March, pp. 591-593 (1977).
Zayed et al., *Pol. J. Pharmacol. Pharm.*, 38, pp. 99-106 (1986).
Kynsh et al., Khimiko-Farmatsevticheskii Zhurnal, 17 pp. 798-801 (1983).
Hazzaa et al., Chemical Abstracts, vol. 90, No. 203971y (1979).
Zayed et al., Chemical Abstracts, vol. 106, No. 156362n (1987).

*Primary Examiner*—Mukund J. Shah
*Assistant Examiner*—E. Bernhardt
*Attorney, Agent, or Firm*—Schweitzer Cornman & Gross

[57] ABSTRACT

The invention relates to new triazolyl quinoline derivatives and acid addition salts thereof wherein $R^1$ stands for hydrogen, methyl, trihalogenomethyl or carboxy;

$R^2$ is hydrogen, halogen, $C_{1-4}$ alkyl, hydroxy, $C_{1-4}$ alkoxy, phenoxy, amino, acetamino, $C_{1-4}$ dialkylamino, acetyl, benzoyl, methylthio, carboxy, cyano, ethoxycarbonyl, nitro or trihalogenomethyl;

$R^3$ represents hydrogen, $C_{1-4}$ alkyl or $C_{1-4}$ alkoxy;

$R^4$ stands for hydrogen, methyl or ethyl and

X stands for a valency bond or —S—.

The new compounds of the general Formula (I)

possess valuable analgesic, antiphlogistic and fungicidal effect and can be used both in therapy and agriculture.

8 Claims, No Drawings

TRIAZOLYL QUINOLINE DERIVATIVES

This is a continuing application of U.S. Ser. No. 006,651, filed as PCT/HU86/00026, May 7, 1986, now abandoned.

This invention relates to new triazolyl quinoline derivatives, a process for the preparation thereof and pharmaceutical and fungicidal compositions containing the same.

According to an aspect of the present invention there are provided new triazolyl quinoline derivatives and acid addition salts thereof wherein $R^1$ stands for hydrogen, methyl, trihalogenomethyl or carboxy;

$R^2$ is hydrogen, halogen, $C_{1-4}$ alkyl, hydroxy, $C_{1-4}$ alkoxy, phenoxy, amino, acetamino, $C_{1-4}$ dialkylamino, acetyl, benzoyl, methylthio, carboxy, cyano, ethoxycarbonyl, nitro or trihalogenomethyl;

$R^3$ represents hydrogen, $C_{1-4}$ alkyl or $C_{1-4}$ alkoxy;

$R^4$ stands for hydrogen, methyl or ethyl and

X stands for a valency bond or —S—.

According to a further aspect of the present invention there is provided a process for the preparation of compounds of the general Formula (I)

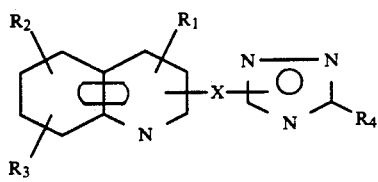
(I)

wherein $R^1$, $R^2$, $R^3$, $R^4$ and X are as stated above and acid addition salts thereof which comprises reacting a halogeno quinoline derivative of the general formula (II)

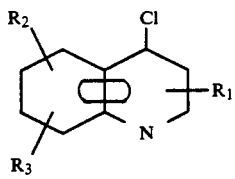
(II)

or

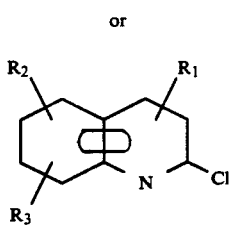
(III)

wherein $R^1$, $R^2$ and $R^3$ are as stated above with a 1,2,4-triazole of the general Formula (IV)

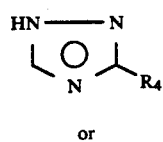
(IV)

or (V)

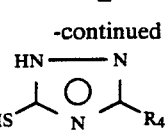
(V)

wherein $R^4$ is as stated above in the presence or absence of a solvent, in the presence or absence of an acid or a base, at a temperature between 0° C. and 200° C. and if desired isolating the product thus obtained in the form of the free base or an acid addition salt thereof.

According to a feature of the process of the present invention there is provided a process for the preparation of compounds of the general Formula (Ia)

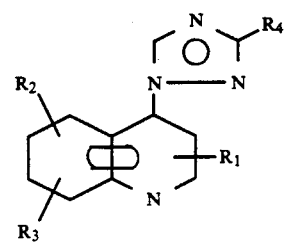
(Ia)

which comprises reacting a 4-chloro-quinoline derivative of the general formula (II) with a 1,2,4-triazole of the general Formula (IV) wherein $R^1$, $R^2$, $R^3$ and $R^4$ are as stated above.

According to a further feature of the process of the present invention there is provided a process for the preparation of compounds of the general Formula (Ib)

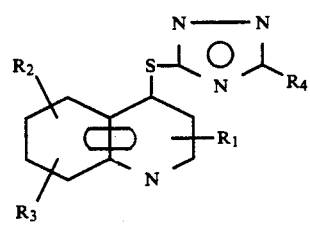
(Ib)

which comprises reacting a 4-chloro-quinoline derivative of the general Formula (II) with a 3-mercapto-1,2,4-triazole of the general Formula (V) wherein $R^1$, $R^2$, $R^3$ and $R^4$ are as stated above.

According to a still further feature of the process of the present invention there is provided a process for the preparation of compounds of the general Formula (Ic)

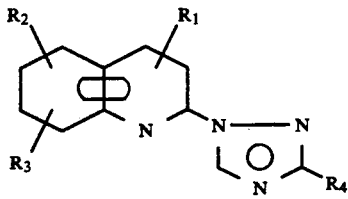
(Ic)

which comprises reacting a 2-chloro-quinoline of the general Formula (III) with a 1,2,4-triazole of the general Formula (IV) wherein $R^1$, $R^2$, $R^3$ and $R^4$ are as stated above.

According to a still further feature of the process of the present invention there is provided a process for the preparation of compounds of the general Formula (Id)

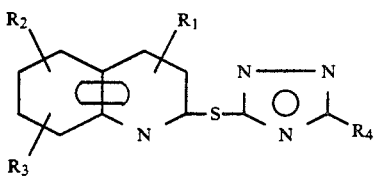
(Id)

which comprises reacting a 2-chloro-quinoline derivative of the general Formula (III) with a 3-mercapto-1,2,4-triazole of the general Formula (V) wherein $R^1$, $R^2$, $R^3$ and $R^4$ are as stated above.

The starting materials used in the process of the present invention are known compounds. The prior art references of the starting materials are as follows:

4-chloro-quinolines of the general Formula (II): "The Chemistry of Heterocyclic Compounds" Vol. 32 Quinolines Part I pages 391-398; the references cited therein; Hungarian patent applications Ser. No. 3869/82 and 4003/82.

2-chloro-quinolines of the general Formula (III): "The Chemistry of Heterocyclic Compounds" Vol. 32 Quinolines Part I pages 387-390: J. Chem. Soc. P.I. 1981 1(5) 1537-1543.

1H-1,2,4-triazoles of the general Formula (IV): Hungarian patent application Ser. No. 4370/83; DOS No. 2,802,491; Chem. Ber. 1968, 101 (6) 2033-2036.

3(5)-mercapto-1,2,4-triazoles of the general Formula (V): Liebigs. Ann. Chem. 637, 133 135-165 (1960).

The new compounds of the general Formula (I) possess valuable biological properties and exhibit useful analgesic and antiphlogistic effect. Some representatives of the compounds of the general Formula (I) are highly active against phytopathogenic fungal pests according to both in vivo and in vitro tests.

It has been found that the reaction between 4- and 2-chloro-quinoline derivatives of the general Formula (II) or (III), respectively, comprising only electron repulsing substituents (e.g. methyl or methoxy groups) and 1H-1,2,4-triazoles or 3(5)-mercapto-1H-1,2,4-triazoles of the general Formula (IV) or (V), respectively, is autocatalytic whereby the hydrochloric acid formed in the course of the reaction acts as catalyst. The reaction can also be catalysed by other acids, particularly strong mineral or organic acids or acidic salts e.g. sulfuric acid, trifluoroacetic acid or ammonium chloride. It is preferred to carry out the reaction in the presence of the said acidic compounds—particularly hydrochloric acid—which can be used in the range of from catalytic to stochiometrical amount.

If less basic chloro quinolines comprising electron attracting group or groups e.g. chlorine, trifluoromethyl are used, such catalysis is not observed. In this case, however, the reaction may be facilitated by carrying out the same in the presence of an organic or inorganic base e.g. triethyl amine, potassium carbonate or sodium hydroxide used in stochiometrical or higher amount. This pertains also to the case if the 1H-1,2,4-triazole or 3(5)-mercapto-1H-1,2,4-triazole derivative is used in the form of an alkali salt e.g. sodium salt thereof.

It has been found furtheron that the mercapto group is more reactive than the —NH—group of the triazole ring.

The reaction preparation of compounds of the general Formulae (Ia), (Ib), (Ic) and (Id) may be carried out preferably in the presence of a polar organic solvent e.g. ethanol, acetone, acetonitrile, dimethyl formamide, dimethyl sulfoxide etc. As reaction medium an apolar organic solvent e.g. benzene, toluene, chloro benzene, dichloro benzene may also be used and one may also work in the absence of an organic solvent in the melt.

The reaction of the present invention may be carried out at a temperature between 0° C. and 200° C., preferably in the range of 20°-150° C. The reaction temperature is selected under taking into consideration the properties of the reactants and the method used.

It is sufficient to react the chloro quinoline component with a molar equivalent amount of the 1H-1,2,4-triazole or 3(5)-mercapto-1,2,4-triazole but the reactions generally take place more rapidly and completely if the starting material of the general Formula (IV) or (V) is used in a 1-2 molar equivalent amount.

According to a form the realization of the process of the present invention the reaction components are melt and the reaction having been terminated the product formed is isolated. According to the said embodiment of the process the product is formed in the form of the hydrochloride thereof. The direct reaction product is treated with an apolar organic solvent e.g. ether, chloroform, benzene, hexane or crystallized from a polar solvent e.g. ethanol, methanol, acetonitrile, dimethyl formamide or a mixture of polar and apolar solvents.

The free base of the general Formula (I) may be isolated by cooling the reaction mixture, dissolving in water or a mixture of water and ethanol—preferably under adding a mineral or organic acid—and precipitating the product by adding an organic or inorganic base. The crude product may be crystallized from a mixture of a polar organic solvent and water or polar and apolar organic solvents.

According to a further embodiment of the process of the present invention the reaction partners are reacted in the presence of an apolar organic solvent e.g. benzene, toluene, xylene, hexane, carbon tetrachloride, chloro benzene, dichloro benzene etc. The reaction having been completed the product precipitated in the form of the hydrochloride is filtered, if necessary crystallized and converted into the free base as described above.

According to a still further embodiment of the process of the present invention the reaction partners are reacted in a polar organic solvent e.g. ethanol, ethylene glycol, acetonitrile, acetone, ethyl methyl ketone, dimethyl formamide, dimethyl sulfoxide, glacial acetic acid. The product is isolated in the form of the free base or a salt formed with a mineral acid.

According to a preferred embodiment of the process of the present invention the reaction is accomplished in a polar organic solvent e.g. ethanol, ethylene glycol, acetonitrile, acetone, methyl ethyl ketone, dimethyl formamide, preferably in the presence of hydrochloric acid.

The acidic medium may be either provided by introducing an acid preferably hydrochloric acid to the reaction mixture or by using the chloro quinoline component in the form of a salt preferably hydrochloride thereof. The product formed in the form of a salt may be isolated from the reaction mixture according to one of the methods set forth above.

According to a further preferable form of realization of the present process of the invention the reaction is accomplished in a polar organic solvent, in the presence of a molar equivalent or larger amount of a strong base e.g. triethyl amine, potassium carbonate, sodium carbonate etc.

The above reaction may also be carried out by using the triazole or mercapto triazole of the general Formula (IV) or (V), respectively, in the form of an alkali e.g. sodium or potassium salt thereof.

The structure of the new compounds prepared by the process of the present invention is characterized and confirmed by means of NMR, IR and MS spectrum and the purity of the product is determined by thin layer, gas and liquid chromatography.

The compounds of the general Formula (I) possess valuable physiological properties and eliminate or efficiently relieve induced pain and inflammation processes. The significant advantage of the compounds of the general Formula (I) is that in analgesic and antiphlogistic dose range ulcerative activity is observed not at all or but to a very small extent.

Thus the orally administered compounds of the general Formula (I) efficiently reduce acute inflammatory processes. According to the method of Winter [Proc. Soc. Exp. Biol. Med. 111, 544 (1962)] carrageenin edema is induced and evaluated on male Wistar rats fasted for 16 hours body weight 160-180 g. Percental inhibition is calculated from the average edema values of the groups treated with the test compound on the one hand and with carrier carboxy methyl cellulose, CMC; control on the other. $ED_{50}$ values are determined by means of regression analysis of the inhibition values. The test compounds are administered through a stomach canule in the form of a 1% carboxy methyl cellulose (CMC) suspension, one hour before introducing the carrageenin injection. The carrageenin edema inhibiting effect of the test compounds are summarized in Table I.

The protecting effect of the test compounds against adjuvant induced arthritis is shown in Table II. According to the method of Newbold 0.1 ml of Freund complet adjuvant (Difco Lab. Mich. U.S.A.) is injected to the plantar surface of the right hind paw of male Wistar rats weighing 160-200 g. The volume of the hind paws is measured before and 21 days after the administration of the adjuvant with the aid of a mercury plethysmometer. The test compound is administered to the test animals for two weeks in a daily oral dose of 25 mg/kg. In Table II the "percental inhibition of the growth of paw volume" relates to the value determined on the 21st day.

In the adjuvant arthritis test, considered to be the best model test of rheumatoidal arthritis, the compounds of the present invention inhibit articular deformations more effectively than the reference substances Naproxen and Phenylbutazon. The tests show furthermore that the compounds of the present invention are active not only in healing morphological deformations but effect in a desirable and useful manner the functional condition and fitness of the feet, moreover the general physical state and condition of the animals, too.

The analgesic effect of the compounds of the present invention is tested according to the hot (56° C.) plate test on male and female CFLP strain mice weighing 18-22 g. The point of time of the appearence of the deterring reaction Abwehrreaktion is determined and related to the latent time measured on the control group Woolfe and McDonald 1944. At least 10 animals are used per dose. The test compounds are administered orally 60 minutes before the test in the form of a 1% methyl cellulose suspension. The results are summarized in Table III. The test is carried out on separated male Wistar rats weighing 180-210 g and fasted for 16 hours. The test compounds are suspended in 1% carboxy methyl cellulose and administered orally in a dose of 10 ml/kg.

Five hours after treatment the animals are sacrificed and their stomachs are placed into a 2.5% formaline solution. The number and rate of punctiform haemorrhage and ulcers is evaluated according to the following scale:

0 = no lesion;
1 = some punctiform haemorrhage ($<10$);
2 = diffuse haemorrhage or small ulcer ($<2$ mm);
3 = two or more minor small ulcer ($<2$ mm);
4 = one or more large ulcer ($>2$ mm).

In a dose of 25 mg/kg and 100 mg/kg the compounds of the present invention do not exhibit ulcerogenic effect. In acute test the $UD_{50}$ value of Naproxen and Indomethacin amounts to 20.8 mg/kg and 6.3 mg/kg p.o., respectively.

The acute toxicity of the compounds of the general Formula (I) is determined according to the method of Litchfield - Wilcoxon on male and female rats of CFLP strain. The $LD_{50}$ values vary between 500 and 2000 mg/kg p.o.

According to a further aspect of the present invention there are provided pharmaceutical compositions comprising in an effective amount at least one compound of the general Formula (I) wherein $R^1$, $R^2$, $R^3$, $R^4$ and X are as stated above or a pharmaceutically acceptable acid addition salt thereof as active ingredient in admixture with suitable inert solid or liquid pharmaceutical carriers.

The pharmaceutical compositions may be prepared in a manner known per se by admixing at least one compound of the general Formula (I) or a pharmaceutically acceptable acid addition salt thereof with suitable inert solid or liquid pharmaceutical carriers.

The compounds of the present invention may be used in therapy preferably for the treatment of various rheumatic diseases, particularly rheumatoidal arthritis, spondylitis, osteoarthritis and gout. The active ingredient may be finished by known methods of pharmaceutical industry in forms suitable for enteral or parenteral administration e.g. tablets, capsules, dragées, injections etc. The pharmaceutical compositions of the present invention may optionally comprise one or more further biologically active materials in addition to the compound of the general Formula (I). The compositions comprise carriers and excipients generally used in therapy.

The dose of the compounds of the general Formula (I) varies between wide ranges and depends on several factors e.g. body weight, age and condition of the patient etc. The dose amounts generally to 10-200 mg/kg body weight enteral administration and to 1-50 mg/kg parenteral administration. The above ranges are, however, just of an informative character.

The compounds of the general Formula (I) possess considerable antifungal activity, too, and are active against phytopathogenic fungal strains and diseases. The compounds of the general Formula (I) are particularly effective against powdery mildew. In Table IV the activity of some compounds of the general Formula (IV) against *Erysiphe graminis* f. sp. tritici strain are disclosed.

The following test method is used: Glasshouse conditions: temperature 20° C.; relative humidity 80%; strength of illumination 6000 lux. The test plants MV-9 Automn wheat are cultivated in pots diameter 20 cm in a 1:1 mixture of sand and perlite. The average number of plants per pot amounts to 180, the height of the plants is 6-7 cm. About 8 ml of the aqueous suspension of the test compound is applied onto the plants with the aid of a sprayer.

The rate of infectedness is determined after 8 days. Activity is calculated from the percental inhibition values. As control commercial products Fundazol 50 WP and Karathene LC 50 are used.

According to a further feature of the present invention there are provided fungicidal compositions comprising as active ingredient in an effective amount at least one compound of the general Formula (I) wherein $R^1$, $R^2$, $R^3$, $R^4$ and X are as stated above or an acid addition salt thereof in admixture with suitable inert solid or liquid carriers or diluents.

The said fungicidal compositions are prepared by methods known per se.

TABLE I

Antiphlogistic effect on carrageenin induced edema on rats

| Test compound No. | Dose mg/kg p.o. | n | Percental inhibition of paw volume | $ED_{50}$ mg/kg p.o. |
|---|---|---|---|---|
| 61 | 12.5 | | 29 | 60.9 |
| | 25.0 | | 37 | |
| | 100.0 | | 58 | |
| 62 | 12.5 | | 18 | 38.4 |
| | 25.0 | | 51 | |
| | 50.0 | | 59 | |
| | 100.0 | | 69 | |
| 64 | 12.5 | | 15 | 59.1 |
| | 25.0 | | 27 | |
| | 50.0 | | 44 | |
| | 100.0 | | 65 | |
| 69 | 12.5 | | 27 | 35.0 |
| | 25 | | 33 | |
| | 50 | | 52 | |
| | 100 | | 86 | |
| 74 | 12.5 | | 26 | 25.7 |
| | 25 | | 55 | |
| | 50 | | 69 | |
| 83 | 12.5 | | 21 | 28.1 |
| | 25 | | 63 | |
| | 50 | | 70 | |
| | 100 | | 72 | |
| 107 | 12.5 | | 29 | 30.6 |
| | 25 | | 40 | |
| | 50 | | 70 | |
| | 100 | | 74 | |
| 108 | 12.5 | 10 | 19 | 38.5 |
| | 25 | 10 | 45 | |
| | 50 | 10 | 61 | |
| | 100 | 10 | 70 | |
| 110 | 12.5 | 10 | 10 | 51.4 |
| | 25 | 10 | 42 | |
| | 50 | 10 | 46 | |
| | 100 | 10 | 61 | |
| Phenylbutazon | 25 | 10 | 21 | 100.9 |
| | 50 | 15 | 42 | |
| | 100 | 15 | 45 | |
| | 200 | 15 | 66 | |
| Naproxen | 12.5 | 15 | 33 | 28.7 |
| | 25 | 15 | 49 | |
| | 50 | 15 | 64 | |
| | 100 | 15 | 71 | |
| Indomethacin | 1 | 10 | 28 | 4.1 |
| | 2 | 10 | 40 | |
| | 4 | 10 | 47 | |
| | 8 | 10 | 64 | |
| | 12 | 10 | 67 | | n = number of the test animals

TABLE II

Inhibitory effect on adjuvant induced arthritis on rats

| Test compound No. | Dose mg/kg p.o. | n | Percental inhibition of the growth of paw volume, on the 21st day |
|---|---|---|---|
| 46 | 25 | 10 | 28.1 |
| 61 | 25 | 10 | 38.2 |
| 62 | 25 | 10 | 40.3 |
| 64 | 25 | 10 | 40.6 |
| 67 | 25 | 10 | 32.8 |
| 69 | 25 | 10 | 35.2 |
| 83 | 25 | 12 | 46.7 |
| 85 | 25 | 12 | 28.4 |
| 107 | 25 | 12 | 17.8 |
| 108 | 25 | 12 | 35.2 |
| 109 | 25 | 12 | 36.7 |
| 110 | 25 | 12 | 32.1 |
| 138 | 25 | 10 | 35.2 |
| Phenylbutazon | 50 | 15 | 18.5 |
| Naproxen | 12.5 | 15 | 16.8 |
| | 25 | 15 | 28.4 | n = number of the test animals

TABLE III

Hot plate test, on mice

| Test compound No. | Dose mg/kg p.o. | Lengthening of reaction time in % |
|---|---|---|
| 46 | 25 | 7 |
| | 50 | 18 |
| | 100 | 38 |
| 61 | 25 | 20 |
| | 50 | 22 |
| | 100 | 26 |
| 62 | 12.5 | 17 |
| | 25 | 19 |
| | 50 | 30 |
| | 100 | 38 |
| 64 | 25 | 17 |
| | 50 | 39 |
| | 100 | 44 |
| 69 | 25 | 13 |
| | 50 | 24 |
| | 100 | 30 |
| 74 | 25 | 19 |
| | 50 | 26 |
| | 100 | 43 |
| 83 | 25 | 16 |
| | 50 | 28 |
| | 100 | 59 |
| 107 | 25 | 34 |
| | 50 | 41 |
| | 100 | 88 |
| 108 | 25 | 34 |
| | 50 | 46 |
| | 100 | 46 |
| 110 | 25 | 21 |
| | 50 | 34 |
| | 100 | 52 |
| 138 | 25 | 25 |
| | 50 | 37 |
| | 100 | 82 |
| Phenylbutazon | 100 | 29 |
| | 150 | 42 |
| | 200 | 44 |
| Naproxen | 12.5 | 25 |
| | 25 | 31 |
| | 50 | 45 |
| | 100 | 49 |

TABLE IV

In vitro antifungal effect on Erysiphe graminis test organism

| Test compound No. | Concentration μg/ml | Inhibition % | $ED_{50}$ μg/ml |
|---|---|---|---|
| 1 | 37.5 | 50.6 | 32.9 |
| | 50 | 72.6 | |
| | 75 | 83.0 | |

TABLE IV-continued

In vitro antifungal effect on *Erysiphe graminis* test organism

| Test compound No. | Concentration µg/ml | Inhibition % | ED$_{50}$ µg/ml |
|---|---|---|---|
| | 100 | 85.3 | |
| | 150 | 36.8 | |
| | 200 | 90.1 | |
| | 400 | 99.6 | |
| 8 | 25 | 42.1 | 31.1 |
| | 50 | 70.9 | |
| | 100 | 82.0 | |
| | 150 | 84.1 | |
| | 200 | 91.9 | |
| | 400 | 98.8 | |
| 10 | 25 | 20.3 | 56.9 |
| | 50 | 42.8 | |
| | 100 | 76.4 | |
| | 200 | 92.7 | |
| | 400 | 90.1 | |
| 6 | 25 | 49.2 | 27.9 |
| | 50 | 71.6 | |
| | 100 | 85.1 | |
| | 200 | 89.5 | |
| | 400 | 99.4 | |
| 22 | 25 | 40.8 | 31.2 |
| | 50 | 67.7 | |
| | 100 | 79.8 | |
| | 200 | 93.0 | |
| | 400 | 96.9 | |
| Karathane LC 50 | 12.5 | 24.9 | 27.4 |
| | 25 | 46.2 | |
| | 50 | 72.7 | |
| | 100 | 87.9 | |
| Chinoin fundazol 50 WP | 50 | 55.3 | 41.2 |
| | 100 | 72.6 | |
| | 200 | 89.1 | |
| | 400 | 94.6 | |

Further details of the present invention are to be found in the following Examples without limiting the scope of protection to the said Examples.

EXAMPLE 1

4-(1H-1,2,4-triazole-1-yl)-7-chloro-quinoline

A mixture of 1.98 g of 4,7-dichloro-quinoline, 1.38 g of 1,2,4-triazole and 10 ml of dimethyl formamide is stirred at 100° C. for 6 hours, whereupon the reaction mixture is poured into 100 ml of water and neutralized with 1 ml of a concentrated ammonium hydroxide solution. The precipitated product is filtered and recrystallized from ethanol. Thus 1.61 g of the desired product are obtained, yield 70%, Mp.: 169°-170° C.

EXAMPLE 2

4-(1H-1,2,4-triazole-1-yl)-2,8-dimethyl-quinoline

A mixture of 1.91 g of 2,8-dimethyl-4-chloro-quinoline and 1.38 g of 1,2,4-triazole is melt at 120° C. and stirred for 2 hours. The solidified melt is dissolved in a mixture of ethanol and water. The solution is poured into a solution of 0.84 g of sodium bicarbonate and 20 ml of water. The precipitated product is filtered. Thus 1.97 g of the desired compound are obtained, yield 88%, m.p.: 99°-100° C.

EXAMPLE 3

4-(1H-1,2,4-triazole-1-yl)-2-methyl-6-methoxy-quinoline

A mixture of 2.44 g of 2-methyl-4-chloro-6-methoxy-quinoline-hydrochloride, 1.38 g of 1,2,4-triazole and 10 ml of dimethyl formamide is stirred at 80° C. for 3 hours whereupon the reaction mixture is poured into 100 ml of water and neutralized with 2 ml of a concentrated ammonium hydroxide solution. The precipitated product is filtered. Thus 2.09 g of the desired compound are obtained, yield 87%, mp.: 117°-118° C.

EXAMPLE 4

4-(1H-1,2,4-triazole-1-yl)-2-methyl-6,8-dichloro-quinoline

A mixture of 2.46 g of 2-methyl-4,6,8-trichloro-quinoline, 1.82 g of the sodium salt of 1,2,4-triazole and 10 ml of dimethyl formamide is stirred at 100° C. for 25 hours whereupon the reaction mixture is poured into 100 ml of water. The precipitated product is filtered. Thus 2.59 g of the desired compound are obtained, yield 93%. Mp.: 220°-222° C.

EXAMPLE 5

4-(1H-1,2,4-triazole-1-yl)-2,8-bis-trifluoromethyl-quinoline

A mixture of 3.0 g of 4-chloro-2,8-bis-trifluoromethyl-quinoline, 1.38 g of 1,2,4-triazole, 1.38 g of potassium carbonate and 30 ml of acetone is heated to boiling for 23 hours whereupon the reaction mixture is poured into 100 ml of water. The precipitated product is filtered, dissolved in 5 ml of ethanol, whereupon 5 ml of water are added. The precipitated product is filtered. Thus 2.42 g of the desired compound are obtained, yield: 73%, mp.: 106°-107° C.

EXAMPLE 6

4-[1H-1,2,4-triazole-3(5)-yl-5(3)-mercapto]-2-trichloromethyl-8-chloro-quinoline A mixture of 3.16 g of 2-trichloromethyl-4,8-dichloro-quinoline, 1.48 g of the sodium salt of 3(5)-mercapto-1,2,4-triazole and 10 ml dimethylformamide is stirred at 100° C. for 18 hours. The reaction having been completed the reaction mixture is poured into water, the precipitated product is filtered and recrystallized from ethanol. Thus 2.1 g of the desired compound are obtained, yield 55%, M.p.: 188°-183° C.

EXAMPLE 7

4-[5(3)-ethyl-1H-1,2,4-triazole-3(5)-yl-mercapto]-2,8-dimethyl-quinoline a mixture of 1.32 g of 4-chloro-2,8-dimethyl-quinoline, 1.55 g of 3(5)-mercapto-5(3)-ethyl-1,2,4-triazole and 20 ml of ethanol is stirred at 30° C. for 20 hours. The reaction mixture is poured into 50 ml of water, neutralized with 1 ml of concentrated ammonium hydroxide and the precipitated product is filtered. Thus 2.41 g of the desired compound are obtained, yield 85%, mp.: 176°-177° C.

EXAMPLE 8

2-(1H-1,2,4-triazole-1-yl)-3-methyl-quinoline

A mixture of 1.78 g of 2-chloro-3-methyl-quinoline and 0.69 g of 1,2,4-triazole is melt and allowed to stand at 120° C. for 4 hours. The melt is cooled, then dissolved in 10 ml of ethanol, poured into 20 ml of water and neutralized with 1 ml of concentrated ammonium hydroxide. The precipitated product is filtered. Thus 1.49 g of the desired compound are obtained, yield 71%. Mp.: 80°-81° C.

EXAMPLE 9

2-(1H-1,2,4-triazole-1-yl)-4-methyl-quinoline hydrochloride

A mixture of 1.78 g of 2-chloro-4-methyl-quinoline, 0.76 g of 1,2,4-triazole and 10 ml of chloro benzene is stirred at 100° C. for 7 hours. The reaction mixture is cooled, the precipitated product is filtered, dissolved in 5 ml of ethanol and precipitated by adding 10 ml of ethyl ether. The precipitated product is filtered. Thus 1.72 g of the desired compound are obtained, yield 70%. Mp.: 193°-194° C.

EXAMPLE 10

2-(1H-1,2,4-triazole-1-yl)-7-chloro-3,8-dimethyl-quinoline

A mixture of 2.26 g of 2,7-dichloro-3,8-dimethyl-quinoline, 1.1 g of the sodium salt of 1,2,4-triazole and 10 ml of dimethyl formamide is stirred at 100° C. for 25 hours. The reaction mixture is poured into 100 ml of water and the precipitated product is filtered. Thus 2.48 g of the desired compound are obtained, yield 96%. Mp.: 147°-148° C.

EXAMPLE 11

2-(3-methyl-1H-1,2,4-triazole-1-yl)-4,6-bis-trichloromethyl-quinoline

A mixture of 3.99 g of 2-chloro-4,6-bis-trichloromethyl-quinoline, 1.26 g of the sodium salt of 3-methyl-1,2,4-triazole and 10 ml of dimethyl formamide is stirred at 100° C. for 20 hours. The reaction mixture is poured into 100 ml of water, the precipitated product is filtered and recrystallized from 10 ml of ethanol. Thus 2.76 g of the desired compound are obtained, yield 62%. M.p.: 169°-170° C.

EXAMPLE 12

2-[5(3)-methyl-1H-1,2,4-triazole-3(5)-yl-mercapto]-3-methyl-quinoline-hydrochloride A mixture of 1.78 g of 2-chloro-3-methyl-quinoline, 1.38 g of 3(5)-mercapto-5(3)-methyl-1,2,4-triazole and 10 ml of chloro benzene is stirred at 100° C. for 2 hours. The reaction mixture is cooled, the precipitated product is filtered and washed with diethyl ether. Thus 2.8 g of the desired compound are obtained, yield 96%, mp.: 190°-192° C.

EXAMPLE 13

2-[1H-1,2,4-triazole-3(5)-yl-mercapto]-4,8-dimethyl-quinoline-hydrochloride

A mixture of 1.92 g of 2-chloro-4,8-dimethyl-quinoline and 1.21 g of 3(5)-mercapto-1,2,4-triazole is melt and allowed to stand at 120° C. for an hour. The cooled reaction mixture is treated with 5 ml of hot ethanol, cooled and filtered. Thus 1.90 g of the desired compound are obtained, yield 65%. Mp.: 201°-202° C.

EXAMPLE 14

4-(1H-1,2,4-triazole-1-yl)-2,8-dimethyl-5-chloro-quinoline

A mixture of 2.26 g of 4,5-dichloro-2,8-dimethyl-quinoline, 1.38 g of 1,2,4-triazole and 0.1 g of 96% sulfuric acid is stirred at 70° C. for 3 hours. The reaction mixture is poured into 50 ml of water and neutralized with 1 ml of a concentrated ammonium hydroxide solution. The precipitated product is filtered and washed with water. Thus 2.0 g of the desired compound are obtained, yield 77.4%. Mp.: 117°-118° C.

EXAMPLE 15

4-[5(3)-methyl-1H-1,2,4-triazole-3(5)-yl-mercapto]-2-methyl-7,8-dichloro-quinoline A mixture of 2.46 g of 2-methyl-4,7,8-trichloro-quinoline, 1.38 g of 3(5)-mercapto-5(3)-methyl-1,2,4-triazole and 10 ml of dimethyl formamide is stirred at 100° C. for 8 hours. The reaction mixture is poured into 100 ml of water, neutralized and the precipitated product is filtered. Thus 3.10 g of the desired compound are obtained, yield 95%. Mp.: 156°-158° C.

EXAMPLE 16

2-(1H-1,2,4-triazole-1-yl)-3-methyl-7-ethyl-quinoline

A mixture of 2.05 g of 2-chloro-3-methyl-7-ethyl-quinoline, 1.05 g of 1,2,4-triazole-hydrochloride, 0.69 g of 1,2,4-triazole and 10 ml of dimethyl formamide is stirred at 100° C. for 6 hours. The reaction mixture is poured into 100 ml of water, neutralized and the crude product is recrystallized from a mixture of ethanol and hexane. Thus 1.52 g of the desired compound are obtained, yield 64%. Mp.: 72°-73° C.

EXAMPLE 17

2-[1H-1,2,4-triazole-3(5)-yl-mercapto]-4-methyl-quinoline

A mixture of 1.78 g of 2-chloro-4-methyl-quinoline, 1.21 g of 3(5)-mercapto-1,2,4-triazole and 10 ml of dimethyl formamide is stirred at 40° C. for 3 hours. The reaction mixture is poured into 100 ml of water, neutralized and filtered. Thus 2.37 g of the desired compound are obtained, yield 98%, m.p.: 96°-98° C.

EXAMPLE 18

3-[5(3)-ethyl-1H-1,2,4-triazole-3(5)-yl-mercapto]-3,8-dimethyl-quinoline 1.91 g of 2-chloro-3,8-dimethyl-quinoline and 1.55 g of 3(5)-mercapto-5(3)-ethyl-1,2,4-triazole are reacted in an analoguous manner to Example 16. The crude product is recrystallized from a mixture of chloroform and ethanol. Thus 1.93 g of the desired compound are obtained, yield 68%, Mp.: 190°-192° C.

Further compounds are prepared in an analoguous manner to the process described in the preceeding Examples. The compounds are disclosed in the following Table V. The number appearing in the column "method" relates to the number of the Example used for the preparation of the compound in caption.

TABLE V

| Compound No. | $R_1$ | $R_2$ | $R_3$ | $R_4$ | Method | Yield (%) | Mp. °C. |
|---|---|---|---|---|---|---|---|
| Compounds of the general Formula (Ia) | | | | | | | |
| 1 | H | 7-Cl | H | H | 1 | 70 | 169–170 |

TABLE V-continued

| Compound No. | R₁ | R₂ | R₃ | R₄ | Method | Yield (%) | Mp. °C. |
|---|---|---|---|---|---|---|---|
| 2 | H | 8-CH₃ | H | H | 1 | 81 | 142–144 |
| 3 | H | 8-CF₃ | H | H | 4 | 75 | 146–147 |
| 4 | 2-CH₃ | H | H | H | 3 | 57 | 88–89 |
| 5 | 2-CH₃ | 6-CH₃ | H | H | 3 | 71 | 110–112 |
| 6 | 2-CH₃ | 8-CH₃ | H | H | 1 | 88 | 98–100 |
| 7 | 2-CH₃ | 6-OCH₃ | H | H | 3 | 87 | 117–118 |
| 8 | 2-CH₃ | 8-OCH₃ | H | H | 3 | 68 | 179–180 |
| 9 | 2-CH₃ | 6-Cl | H | H | 3 | 58 | 173–175 |
| 10 | 2-CH₃ | 8-Cl | H | H | 4 | 97 | 142–144 |
| 11 | 2-CH₃ | 7-CF₃ | H | H | 4 | 93 | 68–70 |
| 12 | 2-CH₃ | 8-CF₃ | H | H | 4 | 86 | 154–156 |
| 13 | 2-CH₃ | 6-OH | H | H | 1 | 40 | 238–240 |
| 14 | 2-CH₃ | 6-COCH₃ | H | H | 1 | 28 | 189–190 |
| 15 | 2-CH₃ | 7-COOCH₃ | H | H | 1 | 49 | 184–186 |
| 16 | 2-CH₃ | 8-CH | H | H | 4 | 57 | 208–210 |
| 17 | 2-CH₃ | 5-Cl | 8-CH₃ | H | 1 | 88 | 113–115 |
| 18 | 2-CH₃ | 6-Cl | 8-CH₃ | H | 4 | 50 | 173–175 |
| 19 | 2-CH₃ | 7-Cl | 8-CH₃ | H | 4 | 98 | 147–149 |
| 20 | 2-CH₃ | 5-Cl | 8-Cl | H | 1 | 74 | 123–124 |
| 21 | 2-CH₃ | 6-Cl | 8-Cl | H | 4 | 93 | 220–222 |
| 22 | 2-CH₃ | 7-Cl | 8-Cl | H | 4 | 93 | 168–170 |
| 23 | 2-CH₃ | 5-Cl | 8-OCH₃ | H | 1 | 59 | 188–190 |
| 24 | 2-CH₃ | 5-CH₃ | 7-CH₃ | H | 1 | 59 | 119–121 |
| 25 | 2-CH₃ | 5-CH₃ | 8-CH₃ | H | 1 | 64 | 120–122 |
| 26 | 2-CH₃ | 6-CH₃ | 8-CH₃ | H | 1 | 66 | 129–131 |
| 27 | 2-CH₃ | 7-CH₃ | 8-CH₃ | H | 1 | 62 | 128–130 |
| 28 | 2-CH₃ | 5-CH₃ | 8-NHCOCH₃ | H | 1 | 57 | 232–234 |
| 29 | 2-CH₃ | 5-CH₃ | 8-NH₂ | H | 1 | 35 | 205–207 |
| 30 | 2-CCl₃ | 6-CH₃ | H | H | 4 | 50 | 102–104 |
| 31 | 2-CCl₃ | 8-CH₃ | H | H | 4 | 61 | 130–132 |
| 32 | 2-CCl₃ | 8-OCH₃ | H | H | 4 | 31 | 169–170 |
| 33 | 2-CCl₃ | 8-Cl | H | H | 5 | 40 | 133–135 |
| 34 | 2-CCl₃ | 6-CCl₃ | H | H | 5 | 47 | 162–163 |
| 35 | 2-CCl₃ | 8-CCl₃ | H | H | 5 | 50 | 157–158 |
| 36 | 2-CCl₃ | 8-CF₃ | H | H | 5 | 47 | 132–133 |
| 37 | 2-CCl₃ | 6-Cl | 8-Cl | H | 5 | 73 | 157–159 |
| 38 | 2-CF₃ | 8-CF₃ | H | H | 5 | 73 | 106–107 |
| Compound of the general Formula (Ib) | | | | | | | |
| 39 | H | 7-Cl | H | H | 7 | 77 | 161–162 |
| 40 | 2-CH₃ | H | H | H | 7 | 66 | 181–182 |
| 41 | 2-CH₃ | 6-CH₃ | H | H | 7 | 59 | 167–169 |
| 42 | 2-CH₃ | 8-CH₃ | H | H | 7 | 71 | 143–145 |
| 43 | 2-CH₃ | 6-OCH₃ | H | H | 7 | 98 | 191–192 |
| 44 | 2-CH₃ | 8-OCH₃ | H | H | 7 | 77 | 186–187 |
| 45 | 2-CH₃ | 6-Cl | H | H | 7 | 68 | 194–195 |
| 46 | 2-CH₃ | 8-Cl | H | H | 7 | 88 | 199–200 |
| 47 | 2-CH₃ | 7-CF₃ | H | H | 7 | 76 | 205–207 |
| 48 | 2-CH₃ | 8-CF₃ | H | H | 7 | 42 | 183–184 |
| 49 | 2-CH₃ | 5-Cl | 8-CH₃ | H | 7 | 78 | 184–186 |
| 50 | 2-CH₃ | 6-Cl | 8-CH₃ | H | 7 | 66 | 197–199 |
| 51 | 2-CH₃ | 7-Cl | 8-CH₃ | H | 7 | 79 | 168–170 |
| 52 | 2-CH₃ | 6-Cl | 8-Cl | H | 7 | 65 | 206–207 |
| 53 | 2-CH₃ | 7-Cl | 8-Cl | H | 7 | 87 | 199–200 |
| 54 | 2-CCl₃ | 6-CH₃ | H | H | 15 | 72 | 127–129 |
| 55 | 2-CCl₃ | 8-CH₃ | H | H | 6 | 40 | 166–168 |
| 56 | 2-CCl₃ | 8-Cl | H | H | 6 | 55 | 188–189 |
| 57 | 2-CCl₃ | 8-CCl₃ | H | H | 6 | 18 | 129–130 |
| 58 | 2-CCl₃ | 8-CF₃ | H | H | 6 | 50 | 190–192 |
| 59 | 2-CCl₃ | 6-Cl | 8-Cl | H | 6 | 48 | 214–215 |
| 60 | 2-CF₃ | 8-CF₃ | H | H | 6 | 24 | 208–210 |
| 61 | H | 7-Cl | H | CH₃ | 7 | 65 | 227–228 |
| 62 | 2-CH₃ | H | H | CH₃ | 15 | 82 | 175–177 |
| 63 | 2-CH₃ | 6-CH₃ | H | CH₃ | 15 | 78 | 181–182 |
| 64 | 2-CH₃ | 8-CH₃ | H | CH₃ | 15 | 85 | 198–200 |
| 65 | 2-CH₃ | 6-OCH₃ | H | CH₃ | 15 | 98 | 192–193 |
| 66 | 2-CH₃ | 8-OCH₃ | H | CH₃ | 15 | 98 | 186–187 |
| 67 | 2-CH₃ | 8-CF₃ | H | CH₃ | 15 | 96 | 180–182 |
| 68 | 2-CH₃ | 6-Cl | 8-CH₃ | CH₃ | 15 | 99 | 207–208 |
| 69 | 2-CH₃ | 7-Cl | 8-CH₃ | CH₃ | 15 | 62 | 191–193 |
| 70 | 2-CH₃ | 6-Cl | 8-Cl | CH₃ | 15 | 38 | 209–211 |
| 71 | 2-CH₃ | 7-Cl | 8-Cl | CH₃ | 15 | 95 | 156–158 |
| 72 | H | 7-Cl | H | CH₂CH₃ | 7 | 79 | 154–156 |
| 73 | 2-CH₃ | H | H | CH₂CH₃ | 7 | 44 | 135–137 |
| 74 | 2-CH₃ | 6-CH₃ | H | CH₂CH₃ | 7 | 36 | 171–172 |
| 75 | 2-CH₃ | 8-CH₃ | H | CH₂CH₃ | 7 | 85 | 176–177 |
| 76 | 2-CH₃ | 6-OCH₃ | H | CH₂CH₃ | 15 | 77 | 168–170 |
| 77 | 2-CH₃ | 8-OCH₃ | H | CH₂CH₃ | 7 | 30 | 171–173 |
| 78 | 2-CH₃ | 8-CF₃ | H | CH₂CH₃ | 15 | 81 | 162–165 |
| 79 | 2-CH₃ | 6-Cl | 8-CH₃ | CH₂CH₃ | 15 | 44 | 191–193 |
| 80 | 2-CH₃ | 7-Cl | 8-CH₃ | CH₂CH₃ | 15 | 72 | 155–156 |

TABLE V-continued

| Compound No. | $R_1$ | $R_2$ | $R_3$ | $R_4$ | Method | Yield (%) | Mp. °C. |
|---|---|---|---|---|---|---|---|
| 81 | 2-$CH_3$ | 6-Cl | 8-Cl | $CH_2CH_3$ | 15 | 85 | 177–178 |
| 82 | 2-$CH_3$ | 7-Cl | 8-Cl | $CH_2CH_3$ | 15 | 32 | 174–174 |
| Compounds of the general Formula (Ic) | | | | | | | |
| 83 | 3-$CH_3$ | H | H | H | 16 | 71 | 79–80 |
| 84 | 3-$CH_3$ | 6-$CH_3$ | H | H | 16 | 68 | 88–90 |
| 85 | 3-$CH_3$ | 7-$CH_3$ | H | H | 16 | 87 | 79–80 |
| 86 | 3-$CH_3$ | 8-$CH_3$ | H | H | 10 | 30 | 99–101 |
| 87 | 3-$CH_3$ | 6-$CH_2CH_3$ | H | H | 16 | 58 | 81–83 |
| 88 | 3-$CH_3$ | 7-$CH_2CH_3$ | H | H | 16 | 64 | 72–73 |
| 89 | 3-$CH_3$ | 8-$CH_2CH_3$ | H | H | 16 | 41 | 79–80 |
| 90 | 3-$CH_3$ | 6-$OCH_3$ | H | H | 10 | 75 | 87–89 |
| 91 | 3-$CH_3$ | 6-Cl | H | H | 10 | 99 | 148–150 |
| 92 | 3-$CH_3$ | 7-Cl | H | H | 10 | 98 | 119–120 |
| 93 | 3-$CH_3$ | 5-$CH_3$ | 7-$CH_3$ | H | 16 | 70 | 137–139 |
| 94 | 3-$CH_3$ | 6-$CH_3$ | 7-$CH_3$ | H | 16 | 62 | 117–119 |
| 95 | 3-$CH_3$ | 5-$CH_3$ | 8-$CH_3$ | H | 16 | 51 | 138–140 |
| 96 | 3-$CH_3$ | 6-$CH_3$ | 8-$CH_3$ | H | 16 | 84 | 126–128 |
| 97 | 3-$CH_3$ | 7-$CH_3$ | 8-$CH_3$ | H | 16 | 76 | 118–119 |
| 98 | 3-$CH_3$ | 6-Cl | 8-$CH_3$ | H | 10 | 90 | 194–195 |
| 99 | 3-$CH_3$ | 7-Cl | 8-$CH_3$ | H | 10 | 96 | 147–148 |
| 100 | 4-$CH_3$ | H | H | H | 16 | 99 | 111–113 |
| 101 | 4-$CH_3$ | 6-$CH_3$ | H | H | 16 | 71 | 134–136 |
| 102 | 4-$CH_3$ | 7-$CH_3$ | H | H | 10 | 66 | 134–135 |
| 103 | 4-$CH_3$ | 8-$CH_3$ | H | H | 10 | 63 | 124–126 |
| 104 | 4-$CH_3$ | 6-$OCH_3$ | H | H | 10 | 71 | 124–126 |
| 105 | 4-$CH_3$ | 7-Cl | H | H | 10 | 66 | 193–195 |
| 106 | 4-$CCl_3$ | 6-$CCl_3$ | H | $CH_3$ | 11 | 62 | 169–170 |
| Compounds of the general Formula (Id) | | | | | | | |
| 107 | 3-$CH_3$ | H | H | H | 17 | 62 | 144–145 |
| 108 | 3-$CH_3$ | 6-$CH_3$ | H | H | 17 | 84 | 165–166 |
| 109 | 3-$CH_3$ | 7-$CH_3$ | H | H | 17 | 99 | 170–171 |
| 110 | 3-$CH_3$ | 8-$CH_3$ | H | H | 18 | 60 | 124–125 |
| 111 | 3-$CH_3$ | 6-$OCH_3$ | H | H | 18 | 51 | 158–160 |
| 112 | 3-$CH_3$ | 6-Cl | H | H | 17 | 80 | 188–190 |
| 113 | 3-$CH_3$ | 7-Cl | H | H | 17 | 80 | 213–215 |
| 114 | 3-$CH_3$ | 6-Cl | 8-$CH_3$ | H | 18 | 60 | 190–192 |
| 115 | 3-$CH_3$ | 7-Cl | 8-$CH_3$ | H | 18 | 68 | 205–206 |
| 116 | 4-$CH_3$ | H | H | H | 17 | 98 | 96–98 |
| 117 | 4-$CH_3$ | 6-$CH_3$ | H | H | 18 | 92 | 125–126 |
| 118 | 4-$CH_3$ | 7-$CH_3$ | H | H | 18 | 74 | 134–136 |
| 119 | 4-$CH_3$ | 8-$CH_3$ | H | H | 18 | 50 | 135–137 |
| 120 | 4-$CH_3$ | 6-$OCH_3$ | H | H | 18 | 81 | 152–154 |
| 121 | 4-$CH_3$ | 7-Cl | H | H | 18 | 83 | 158–160 |
| 122 | 3-$CH_3$ | H | H | $CH_3$ | 17 | 84 | 211–212 |
| 123 | 3-$CH_3$ | 6-$CH_3$ | H | $CH_3$ | 18 | 74 | 215–216 |
| 124 | 3-$CH_3$ | 7-$CH_3$ | H | $CH_3$ | 17 | 85 | 204–205 |
| 125 | 3-$CH_3$ | 8-$CH_3$ | H | $CH_3$ | 18 | 74 | 212–213 |
| 126 | 3-$CH_3$ | 6-$OCH_3$ | H | $CH_3$ | 18 | 72 | 205–207 |
| 127 | 3-$CH_3$ | 6-Cl | H | $CH_3$ | 18 | 79 | 213–215 |
| 128 | 3-$CH_3$ | 7-Cl | H | $CH_3$ | 18 | 74 | 205–206 |
| 129 | 3-$CH_3$ | 6-Cl | 8-$CH_3$ | $CH_3$ | 18 | 40 | 226–227 |
| 130 | 3-$CH_3$ | 7-Cl | 8-$CH_3$ | $CH_3$ | 18 | 87 | 228–230 |
| 131 | 4-$CH_3$ | H | H | $CH_3$ | 17 | 78 | 172–174 |
| 132 | 4-$CH_3$ | 6-$CH_3$ | H | $CH_3$ | 18 | 74 | 189–190 |
| 133 | 4-$CH_3$ | 7-$CH_3$ | H | $CH_3$ | 18 | 59 | 172–174 |
| 134 | 4-$CH_3$ | 8-$CH_3$ | H | $CH_3$ | 18 | 67 | 188–190 |
| 135 | 4-$CH_3$ | 6-$OCH_3$ | H | $CH_3$ | 17 | 86 | 192–193 |
| 136 | 4-$CH_3$ | 7-Cl | H | $CH_3$ | 17 | 79 | 179–180 |
| 137 | 3-$CH_3$ | H | H | $CH_2CH_3$ | 17 | 85 | 187–189 |
| 138 | 3-$CH_3$ | 6-$CH_3$ | H | $CH_2CH_3$ | 18 | 68 | 209–211 |
| 139 | 3-$CH_3$ | 7-$CH_3$ | H | $CH_2CH_3$ | 17 | 57 | 145–146 |
| 140 | 3-$CH_3$ | 8-$CH_3$ | H | $CH_2CH_3$ | 18 | 68 | 190–192 |
| 141 | 3-$CH_3$ | 6-$OCH_3$ | H | $CH_2CH_3$ | 17 | 67 | 192–195 |
| 142 | 3-$CH_3$ | 6-Cl | H | $CH_2CH_3$ | 18 | 67 | 203–205 |
| 143 | 3-$CH_3$ | 7-Cl | H | $CH_2CH_3$ | 17 | 73 | 191–193 |
| 144 | 3-$CH_3$ | 6-Cl | 8-$CH_3$ | $CH_2CH_3$ | 18 | 50 | 185–186 |
| 145 | 3-$CH_3$ | 7-Cl | 8-$CH_3$ | $CH_2CH_3$ | 18 | 72 | 214–215 |
| 146 | 4-$CH_3$ | H | H | $CH_2CH_3$ | 17 | 92 | 130–131 |
| 147 | 4-$CH_3$ | 6-$CH_3$ | H | $CH_2CH_3$ | 18 | 37 | 132–133 |
| 148 | 4-$CH_3$ | 7-$CH_3$ | H | $CH_2CH_3$ | 18 | 60 | 117–118 |
| 149 | 4-$CH_3$ | 8-$CH_3$ | H | $CH_2CH_3$ | 18 | 63 | 154–156 |
| 150 | 4-$CH_3$ | 6-$OCH_3$ | H | $CH_2CH_3$ | 18 | 40 | 163–165 |
| 151 | 4-$CH_3$ | 7-Cl | H | $CH_2CH_3$ | 18 | 63 | 149–152 |

What we claim is:
1. Triazolyl quinoline compound of the formula

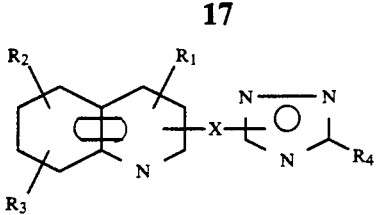

(I)

wherein $R^1$ is methyl, trihalogenomethyl or carboxy;

$R^2$ is hydrogen, halogen, $C_{1-4}$ alkyl, hydroxy, $C_{1-4}$ alkoxy, phenoxy, amino, acetamino, $C_{1-4}$ dialkylamino, acetyl, benzoyl, methylthio, carboxy, cyano, ethoxycarbonyl, nitro or trihalogenomethyl;

$R^3$ is hydrogen, $C_{1-4}$ alkyl or $C_{1-4}$ alkoxy;

$R^4$ is hydrogen, methyl or ethyl; and

X is a valency bond, or —S—, wherein the triazole is attached through a C—N or C—S bond to the 2- or 4-position of the quinoline ring;

and pharmaceutically acceptable acid addition salts thereof, provided that when the triazole is attached through a C—S bond to the 2-position of the quinoline ring, then $R^4$ is not methyl, and $R^1$ is in the 3-position of the quinoline ring.

2. Compound according to claim 1 of the Formula (Ia)

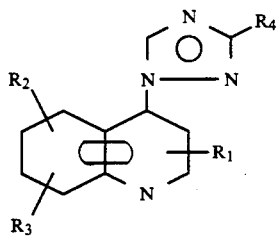

(Ia)

wherein $R^1$, $R^2$, $R^3$ and $R^4$ are as stated in claim 1 and pharmaceutically acceptable acid addition salts thereof.

3. Compound according to claim 1 of the Formula (Ib)

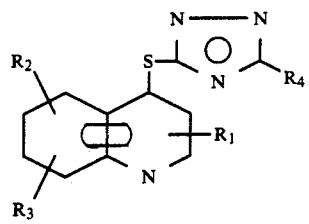

(Ib)

wherein $R^1$, $R^2$, $R^3$ and $R^4$ are as stated in claim 1 and pharmaceutically acceptable acid addition salts thereof.

4. Compound according to claim 1 of the Formula (Ic)

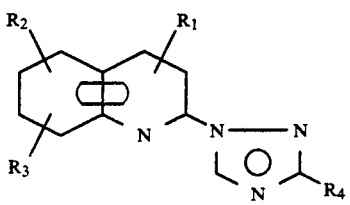

(Ic)

wherein $R^1$, $R^2$, $R^3$ and $R^4$ are as stated in claim 1 and pharmaceutically acceptable acid addition salts thereof.

5. Compound according to claim 1 of the Formula (Id)

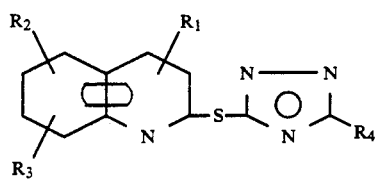

(Id)

wherein $R^1$, $R^2$, $R^3$ and $R^4$ are as stated in claim 1 and pharmaceutically acceptable acid addition salts thereof.

6. Pharmaceutical composition having analgetic and antiphlogistic effect comprising an effective amount of a compound of the Formula (I) wherein $R^1$, $R^2$, $R^3$, $R^4$ and X are as stated in claim 1 or a pharmaceutically acceptable acid addition salt thereof as active ingredient in admixture with suitable inert solid or liquid pharmaceutical carriers.

7. Phytopathogenically fungicidal composition comprising as active ingredient an effective amount of a compound of the Formula (I) wherein $R^1$, $R^2$, $R^3$, $R^4$ and X are as stated in claim 1 or an acid addition salt thereof in admixture with suitable inert solid or liquid carriers or diluents.

8. A method for combating fungal diseases which comprises applying an effective amount of a fungicidal composition according to claim 7 onto the plant.

* * * * *